United States Patent
Hansen et al.

(10) Patent No.: US 6,357,440 B1
(45) Date of Patent: *Mar. 19, 2002

(54) PLIABLE RESPIRATORY MASK

(75) Inventors: Gary L. Hansen, Eden Prairie, MN (US); Nicole Denise Bloom, San Francisco, CA (US)

(73) Assignee: Mallinckrodt Inc., St. Louis, MO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/333,682

(22) Filed: Jun. 16, 1999

(51) Int. Cl.[7] .................................................. A62B 7/10
(52) U.S. Cl. .............................. 128/206.19; 128/206.18
(58) Field of Search ...................... 128/206.12, 206.13, 128/206.16, 206.19, 206.18, 206.21, 206.27, 206.28, 207.13, 207.11, 207.17, 863

(56) References Cited

U.S. PATENT DOCUMENTS

| | | | | | |
|---|---|---|---|---|---|
| 781,516 A | * | 1/1905 | Guthrie, Jr. | ............. | 128/207.13 |
| 838,434 A | * | 12/1906 | Morgan | .................. | 128/207.13 |
| 2,284,949 A | * | 6/1942 | Cover | .......................... | 128/148 |
| 2,859,748 A | * | 11/1958 | Hudson | ........................ | 128/146 |
| 2,902,032 A | * | 9/1959 | Davis | .......................... | 128/145 |
| 2,939,458 A | * | 6/1960 | Lundquist | .............. | 128/206.12 |
| 3,664,335 A | * | 5/1972 | Boucher et al. | ......... | 128/146.6 |
| 3,695,264 A | * | 10/1972 | Laeral | ...................... | 128/145.5 |
| 4,002,167 A | | 1/1977 | Rambosek | | |
| 4,041,203 A | * | 8/1977 | Brock et al. | ................. | 428/157 |
| 4,266,540 A | * | 5/1981 | Panzik et al. | .......... | 128/207.13 |
| 4,328,797 A | | 5/1982 | Rollins, III et al. | | |
| 4,337,767 A | * | 7/1982 | Yahata | .................. | 128/206.28 |
| 4,354,488 A | * | 10/1982 | Bartos | .................. | 128/205.25 |
| 4,361,146 A | * | 11/1982 | Woicke | ................. | 128/206.12 |
| 4,412,537 A | * | 11/1983 | Tiger | ..................... | 128/204.17 |
| 4,469,097 A | * | 9/1984 | Kelman | .................. | 128/205.22 |
| 4,643,182 A | * | 2/1987 | Klein | ..................... | 128/201.25 |
| 4,803,981 A | * | 2/1989 | Vickery | .................. | 128/207.13 |
| 4,846,170 A | * | 7/1989 | McAnalley et al. | ... | 128/207.13 |
| 4,848,366 A | * | 7/1989 | Aita et al. | ................... | 128/863 |
| 4,883,052 A | * | 11/1989 | Weiss et al. | ........... | 128/206.12 |
| 4,944,310 A | * | 7/1990 | Sullivan | ................. | 182/207.13 |
| 5,018,519 A | * | 5/1991 | Brown | .................. | 128/203.29 |
| RE35,339 E | * | 10/1996 | Rapoport | ............. | 128/204.18 |
| 5,590,646 A | * | 1/1997 | Murphy | .................. | 182/206.19 |
| 5,657,752 A | * | 8/1997 | Landis et al. | .......... | 128/207.13 |
| 5,681,645 A | * | 10/1997 | Strack et al. | ............... | 428/196 |
| 5,704,349 A | * | 1/1998 | Hubbard et al. | ....... | 128/206.19 |
| 5,746,201 A | * | 5/1998 | Kidd | ..................... | 128/206.24 |
| 5,753,373 A | * | 5/1998 | Scholz et al. | ............... | 428/429 |
| 5,762,643 A | * | 6/1998 | Ray et al. | ................... | 604/383 |
| 5,834,386 A | * | 11/1998 | Cohen | .................... | 128/206.21 |
| 5,857,460 A | * | 1/1999 | Popitz | .................... | 128/206.21 |
| 6,192,886 B1 | * | 2/2000 | Rudolph | ................. | 128/207.13 |
| 6,109,263 A | * | 8/2000 | Feuchtgruber | ......... | 128/206.28 |
| 6,112,746 A | * | 9/2000 | Kwok et al. | ........... | 128/207.13 |
| 6,237,596 B1 | * | 5/2001 | Bohmfalk | .............. | 128/206.22 |

FOREIGN PATENT DOCUMENTS

| | | |
|---|---|---|
| EP | 0350914 | 1/1990 |
| WO | 9705919 | 2/1997 |

* cited by examiner

*Primary Examiner*—John G. Weiss
*Assistant Examiner*—Teena Mitchell
(74) *Attorney, Agent, or Firm*—Rothwell, Figg, Ernst & Manbeck

(57) ABSTRACT

A pliable respiratory mask is provided according to the invention. The pliable respiratory mask includes a mask shell adapted to fit over a portion of a face of a person, the mask shell being formed of a pliable material selected from the group consisting of a woven fabric, a non-woven fabric, a non-woven paper, or a pliable foam material, a hose connector extending through the pliable material of the mask shell and fastened to the pliable material, and an attachment for securing the shell over a portion of the person's face.

8 Claims, 2 Drawing Sheets

PLIABLE RESPIRATORY MASK

BACKGROUND OF THE INVENTION

1. Field of the Invention

The present invention relates generally to the field of respiratory masks.

2. Description of the Background Art

A respiratory mask is a device used to deliver a gas or gases to a person. In its simplest form, the respiratory mask includes a shell, an attaching means, and a gas supply hose. The respiratory mask may be used to deliver any variety of gases, including air or oxygen, and a variety of medicines or treatments.

The shell is fitted over a nose portion of the face of the person in order to supply a gas to a respiratory system of the person. Related art masks typically have been constructed with the shell being formed of a relatively rigid material.

However, the respiratory mask of the related art has several drawbacks. First, the rigid shell may form a poor seal with the face of the person. Leakage of the supplied gas may be critical in applications where a specific amount of gas must be measured and delivered. Second, the rigid shell may not accommodate differences in the shape or size of features, causing gas leakage and a painful or uncomfortable fit. This may include undesirable pressure points. Third, the rigid shell of the related art is moisture impermeable, and therefore may trap and retain moisture such as perspiration or exhaled vapor. The trapped moisture may contribute to a perception of hotness of the mask, and may lead to discomfort. In addition, any perspiration generated under the edges of the mask is not transported away, and may lead to slipping of the mask or chafing and irritation. Fourth, the related art respiratory mask employs a vent hole by which a constant pressure is maintained in the mask by allowing exhaled air to be vented and flushed out by the supplied gas. This may create a jet of air that may cause discomfort for nearby persons, as well as for the mask wearer.

Therefore, there remains a need in the art for an improved respiratory mask.

SUMMARY OF THE INVENTION

A pliable respiratory mask is provided according to a first aspect of the invention. The pliable respiratory mask comprises a mask shell adapted to fit over a respiratory orifice on a portion of a face of a person, the mask shell being formed of a pliable material selected from the group consisting of a woven fabric, a non-woven fabric, a non-woven paper, or a pliable foam material, a hose connector extending through the pliable material of the mask shell and fastened to the pliable material, and an attaching means.

A pliable respiratory mask is provided according to a second aspect of the invention. The pliable respiratory mask comprises a mask shell adapted to fit over a portion of a face of a person, the mask shell being formed of a pliable material selected from the group consisting of a woven fabric, a non-woven fabric, a non-woven paper, or a pliable foam material, a hose connector extending through the pliable material of the mask shell and fastened to the pliable material, an impermeable coating over a predetermined portion of the mask shell, and an attaching means.

The above and other features and advantages of the present invention will be further understood from the following description of the preferred embodiment thereof, taken in conjunction with the accompanying drawings.

DETAILED DESCRIPTION OF THE PREFERRED EMBODIMENTS

Figure 1:
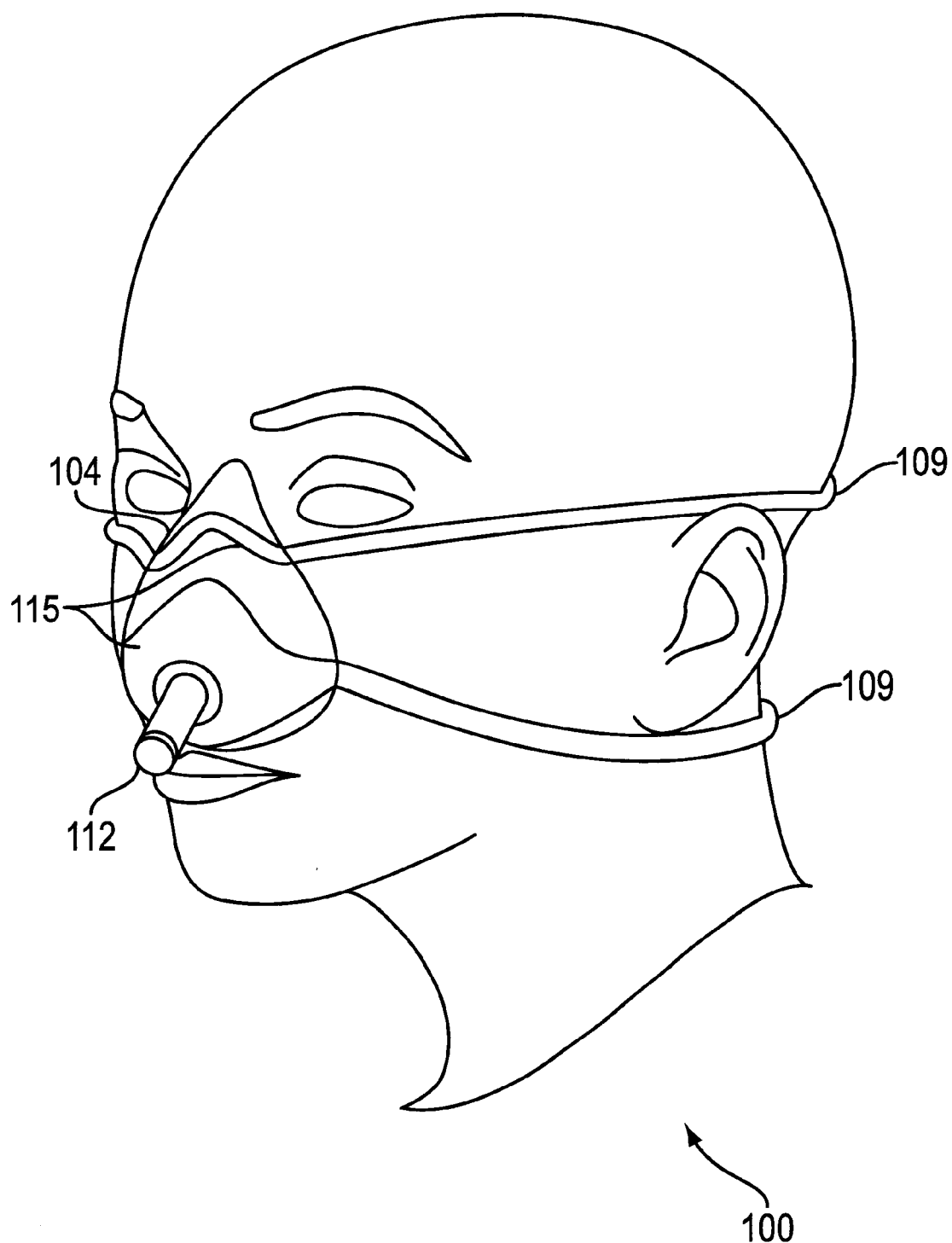
FIG. 1 shows a respiratory mask of the present invention.

FIG. 1 shows a respiratory mask 100 of the present invention. The respiratory mask includes a mask shell 104, an attaching means 109, a hose connector 112, and an impermeable coating 115 extending over a predetermined portion or portions of the mask shell 104.

The mask shell 104 is constructed from a permeable material, including, for example, a woven fabric, a non-woven fabric, a non-woven paper, or a pliable foam material (such as foam rubber). The woven or non-woven fabric includes natural fabrics such as cotton and man-made fabrics such as polyester. The mask shell 104 is of a suitable size to surround and enclose the nose area, but could alternatively be of a size to enclose the mouth area, or both the nose and mouth. Due to the pliable nature of the material, the mask shell 104 conforms to the face of the person, regardless of the shape or size of the person's features. The permeability of the material of the mask shell 104 allows venting of exhaled air and venting of excess supplied gas and expired $CO_2$. The vented air forms a diffuse pattern that is less annoying than a jet of air from a small vent hole. The permeability of the material of the mask shell 104 also allows moisture to pass through. This is significant because moisture or humidity buildup in a respiratory mask often causes the wearer to feel hot. In addition, the permeability of the material may transport moisture, such as perspiration, away from the skin of the wearer. This prevents further discomfort by the wearer.

The attaching means 109 in the preferred embodiment is a pair of elastic straps 109. Alternatively, one such strap may be used if desired, but two straps form a more stable positioning of the mask 100 on the face of the person.

The hose connector 112 extends through the mask shell 104 and is attached thereto. The hose connector 112 is essentially a stub of pipe, to which a gas supply hose may be attached.

The impermeable coating 115 extends over a predetermined portion or portions of the mask shell 104. In the preferred embodiment, the impermeable coating is a flexible plastic. The impermeable coating 115 reduces the available venting area of the mask shell 104, in exchange for some rigidity in the mask 100. In the preferred embodiment, the attaching means 109 is affixed to the mask shell 104 at areas covered by the impermeable coating 115. The pattern shown in the figure is only illustrative, and it is desired to claim any conceivable pattern of the impermeable coating 115.

Figure 2:
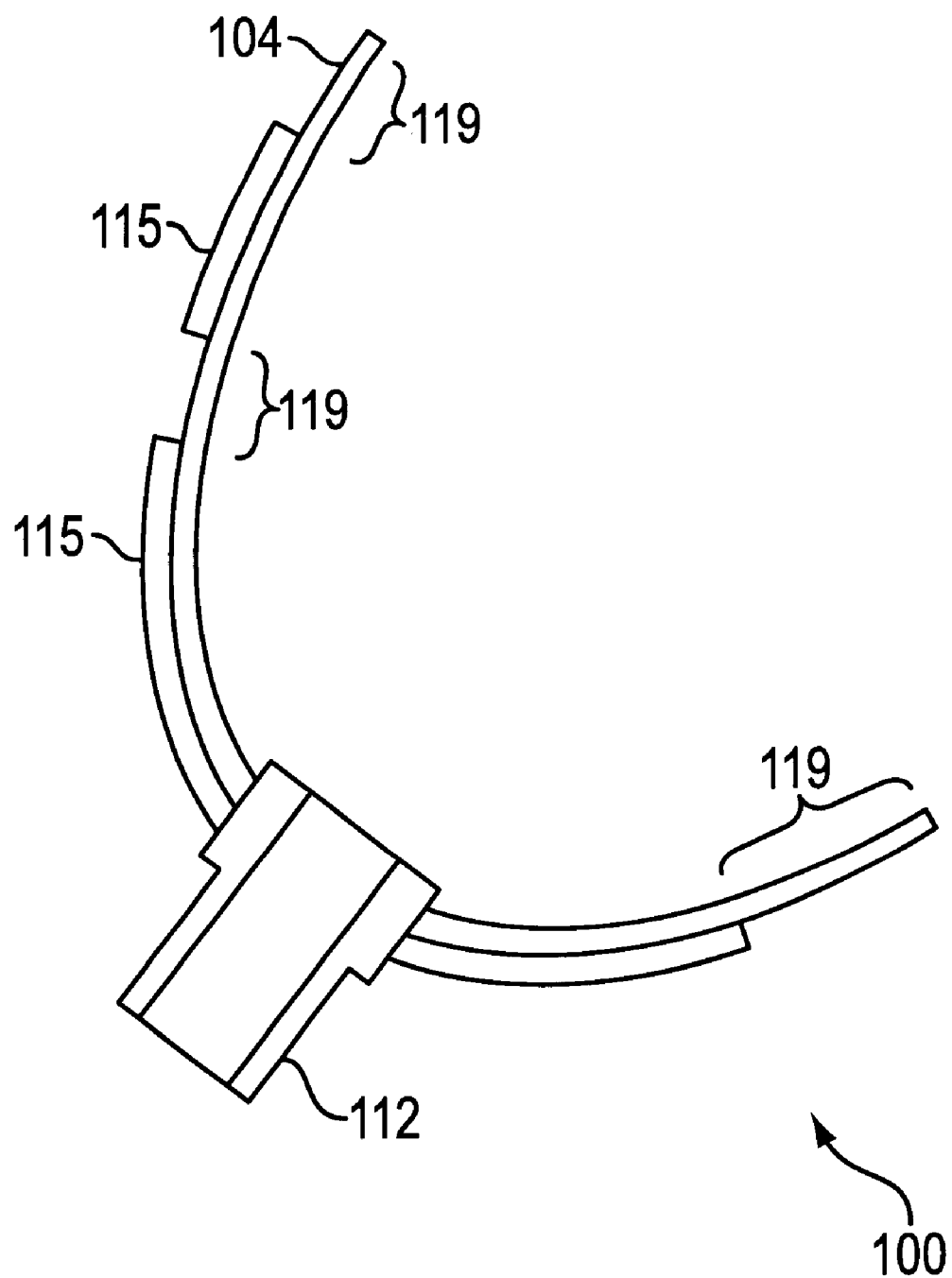
FIG. 2 shows a cross-section of the respiratory mask.

FIG. 2 shows a cross-section of the mask 100, illustrating the vent portions 119 through which exhaled air or a supplied gas may escape from the mask 100. It can be seen that the periphery of the mask shell 104 in the preferred embodiment comprises vent portions 119 and is not coated by the impermeable coating 115.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A pliable respiratory mask, comprising:

a mask shell adapted to fit over a respiratory orifice on a portion of a face of a person, said mask shell being formed of a pliable gas permeable material selected from the group consisting of a woven fabric, a non-woven fabric, a non-woven paper, or a pliable foam material, said pliable gas permeable material defining a vent portion through which exhaled air may escape from the mask, said vent portion being the only form of vent;

a hose connector extending through said pliable material of said mask shell and fastened to said pliable material;

at least one attaching member for securing the mask shell over a portion of the person's face; and a gas impermeable coating extending over a portion of said mask shell, wherein portions of said pliable gas permeable shell material are left uncoated to define vent portions through which exhaled air may escape from said mask.

2. The respiratory mask of claim 1, wherein said attaching member comprises at least one elastic strap.

3. The respiratory mask of claim 1 wherein the portion of the person's face that the mask shell is adapted to fit over is a nose.

4. A pliable respiratory mask, comprising:

a mask shell adapted to fit over a portion of a face of a person, said mask shell being formed of a pliable gas permeable material selected from the group consisting of a woven fabric, a non-woven fabric, a non-woven paper, or a pliable foam material;

a hose connector extending through said pliable material of said mask shell and fastened to said pliable material;

a gas impermeable coating over a predetermined portion of said mask shell; and at least one attaching member for securing the mask shell over a portion of the person's face.

5. The respiratory mask of claim 4, wherein said attaching member comprises at least one elastic strap.

6. The respiratory mask of claim 4 wherein the portion of the person's face that the mask shell is adapted to fit over is a nose.

7. The respiratory mask of claim 4 wherein said hose connector extends through a portion of said mask shell coated with said gas impermeable coating.

8. The respiratory mask of claim 4 wherein said attaching member is affixed to said mask at areas coated with said gas impermeable coating.

* * * * *